(12) United States Patent
Litz et al.

(10) Patent No.: US 6,197,983 B1
(45) Date of Patent: Mar. 6, 2001

(54) GERMANES AND DOPING WITH GERMANES

(75) Inventors: Kyle Erik Litz, Ballston Spa, NY (US); Mark M. Banaszak Holl, Ann Arbor; John E. Bender, IV, Allendale, both of MI (US)

(73) Assignee: The Regents of the University of Michigan, Ann Arbor, MI (US)

(*) Notice: Subject to any disclaimer, the term of this patent is extended or adjusted under 35 U.S.C. 154(b) by 0 days.

(21) Appl. No.: 09/254,338
(22) PCT Filed: Sep. 5, 1996
(86) PCT No.: PCT/US96/14342
    § 371 Date: Jul. 19, 1999
    § 102(e) Date: Jul. 19, 1999
(87) PCT Pub. No.: WO98/10463
    PCT Pub. Date: Mar. 12, 1998
(51) Int. Cl.[7] ................ C07F 7/22; C07F 7/08; H01L 21/22
(52) U.S. Cl. .................. 556/12; 556/81; 438/542
(58) Field of Search .......... 556/12, 81; 438/542

(56) References Cited

U.S. PATENT DOCUMENTS

| | | | |
|---|---|---|---|
| 2,854,366 | * 9/1958 | Wannlund, Jr. et al. | 148/1.5 |
| 3,615,856 | * 10/1971 | Sommers, Jr. | 136/89 |
| 4,357,183 | * 11/1982 | Fan et al. | 148/181 |
| 5,158,656 | * 10/1992 | Ayers | 204/101 |

* cited by examiner

Primary Examiner—Edna Wong
(74) Attorney, Agent, or Firm—Medlen & Carroll, LLP

(57) ABSTRACT

The present invention provides germanium-containing compounds which can function as dopants and where the methods for their use are flexible, reliable and environmentally safe. The process includes the ability to make bisamidegermanes under relatively mild conditions, usually standard temperature and pressure, without toxic by-products, giving pure products at satisfactory yields.

20 Claims, 2 Drawing Sheets

GERMANES AND DOPING WITH GERMANES

FIELD OF THE INVENTION

The present invention relates to novel germanium-containing compounds and methods of using germanium-containing compounds. In particular, the present invention involves novel germanes and doping silicon-containing substrates, including polycrystalline silicon, with novel germanes.

BACKGROUND

Oxidation of a crystalline silicon substrate results in the formation of a layer of silicon dioxide on the substrate surface. Photolithography can then be used to selectively pattern and etch the silicon dioxide layer to expose a portion of the underlying substrate. These openings in the silicon dioxide layer allow for the introduction ("doping") of ions ("dopant") into defined areas of the underlying silicon. The silicon dioxide acts as a mask; that is, doping only occurs where there are openings. Careful control of the doping process and of the type of dopant allows for the creation of localized areas of different electrical resistivity in the silicon. The particular placement of acceptor ion-doped (positive free hole, "p") regions and donor ion-doped (negative free electron, "n") regions in large part defines the interrelated design of the transistors, resistors, capacitors and other circuit elements on the silicon wafer. Electrical interconnection and contact to the various p or n regions that make up the integrated circuit is made by a deposition of a thin film of conductive material, usually aluminum or polysilicon, thereby finalizing the design of the integrated circuit.

Where it is desired to have semiconductor devices with uncommitted logic gates such that the final logic configuration of the device is determined by the end user, the fabrication process must allow for programming of the device. Programming normally involves adjusting threshold voltages of particular gate transistors located either in or out of a memory row and column matrix. Threshold reduction is achieved by doping the region of the selected depletion devices utilizing ions of a conductivity type the same as that of the MOS transistor's source and drain. Threshold increases are achieved by introducing into the channel region ions of a conductivity type opposite to that of the MOS transistor's source and drain.

Programming methods typically utilize ion implantation to adjust the channel voltage thresholds. In general, the variations among these programming methods involve the number of layers through which ion implantation is performed. In one case, for example, very high energy ion implantation is performed to penetrate the various layers. In another case, low energy ion implantation is performed after etching a deep hole in the deposited layers.

There are a number of types of ions used in such processes; boron is very commonly used. On the other hand, germanium ions have been used; U.S. Pat. No. 5,347,151 to Shirnizu et al, hereby incorporated by reference, describes the implantation of germanium ions under the conditions of the implantation energy 100 KEV and the dose $1 \times 10^{16}$ cm$^{-2}$. Germanium has also been used to enhance doping with n-type dopants; the use of low-pressure vapor deposition of a germanium containing gas into the silicon layer is described in U.S. Pat. No. 5,316,958 to Meyerson, which is hereby incorporated by reference.

There are a number of problems with the ion implantation approach to programming. Most importantly, there is the problem of metallization over the region to be doped. Metallization will block and prevent proper ion implantation. Furthermore, even if metallization can be avoided in the physical area of ion implant, achieving doping at the required depth requires an ion implantation instrument with very high ion beam energy and high through put capacity. Ion implant equipment required to meet these requirements is expensive.

Additionally, vapor deposition of germanium has been used for doping materials in the field of fiber optic cable. For example, fused silica or multicomponent glasses are formed into cable by a "vapor phase process." In this process, $SiCl_4$ is introduced as a vapor and oxidized in a flame to form $SiO_2$ vapor. This vapor is then deposited upon a glass or graphite "bait rod" to form a fiber optic cable. Similarly, $GeCl_4$ is oxidized in flame, forming $GeO_2$ vapor to be deposited in the bait rod to serve as a dopant to change the forming fiber optic cable's index of refraction. [See J. P. Powers, *An Introduction to Fiber Optic Systems*, R. D. Irwin & Asken Assoc., Inc. Boston, Mass. (1993) pp. 459–468.]

This process for doping has a number of disadvantages. Most importantly, applying $GeCl_4$ results in the formation of some environmentally hazardous and unsafe byproducts including HCl, and chlorine gas. Given these problems, it is important to prepare new germanium-containing compounds which can function as dopants and where the methods for their use are flexible, reliable and environmentally safe.

SUMMARY OF THE INVENTION

The present invention relates to novel germanium-containing compounds and methods of using germanium-containing compounds. In particular, the present invention involves novel germanes and doping silicon-containing substrates, including polycrystalline silicon, with novel germanes.

The invention is also directed to the preparation of bisamidegermanes of high purity. The present invention provides a process for the preparation of bisamidegermanes (or organogermanes) which process comprises contacting bisamidegermylenes (whether stable germylenes, or those generated in situ) with a catalyst in the presence of hydrogen. The bisamidegermanes of the present invention are of the general formula $H_2Ge(NR_2)_2$, wherein R=alkyl, aryl, alkylaryl, trialkylsilyl, and the like. The process involves using transition metal catalysts of either, or a combination of Co, Rh, Ir, Ni, Pd, and Pt with dihydrogen in contact with a bisamidegermylene. The process involves utilizing these readily obtainable transition-metal reagents in very small amounts which can be continually re-used until contaminated.

The amide groups of the germanes of the present invention can be easily replaced by carbon-based substituents, or they can be readily hydrolyzed forming condensation products having [—Ge—O—Ge—O] linkages similar to silicone polymers. The bisamidegermanes of the present invention are useful for doping substrates, including the silicon-containing substrates of the microelectronics industry. The present invention contemplates coating such substrates with one or more germanes, as well as utilizing germanes as a chemical vapor deposition (CVD) reagent for the manufacture of amorphous Ge—N in vacuo. The incorporation of germanium into metal-oxide semiconductors increases their operating frequency giving faster devices.

In one embodiment, the present invention contemplates a method of doping a silicon-containing substrate, comprising exposing a liquid germane to a dry silicon-containing substrate, under conditions such that a doped substrate is produced. In a preferred embodiment, the silicon-containing substrate comprises silicon dioxide and the germane is a bisamidegermane of the general formula: $H_2Ge(NR_2)_2$, wherein R=alkyl, aryl, alkylaryl, or trialkylsilyl (such as trimethylsilyl).

The doped substrate can be subjected to further processing steps. In one embodiment, the method further comprises the step of separating said doped substrate from said (unreacted) liquid germane so as to create a treated substrate. It is not intended that the present invention be limited by the manner in which unreacted germane is separated. In one embodiment, the separating is achieved by washing said doped substrate with a solvent (such as benzene). The treated substrate can then be further processed. In one embodiment, the treated substrate is subjected to heating and processed into fibers for a fiber optic device.

DEFINITIONS

The following definitions are provided for the terms used herein:

"Chemical reactions" means reactions involving chemical reactants, such as inorganic compounds.

"Initiating a reaction" means causing a reaction to take place. Reactions can be initiated by any means (e.g. heat, wavelengths of light, addition of a catalyst, etc.)

"Wilkinson's catalyst" is a widely used catalyst for homogenous hydrogenation. As a complex of the transition metal rhodium, its formula is $RhCl(PPh_3)_3$, where Ph stands for phenyl ($C_6H_5$). In solution, Wilkinson's catalyst is believed to exchange reversibly one $Ph_3P$ for a loosely held solvent molecule. Subsequently, the catalyst is brought into contact with the reactants (an alkene and molecular hydrogen) to form a dihydrido complex. The H—H bond is broken, and each hydrogen bonds seperately to rhodium. Then the alkene reacts with the complex and forms an alkene metal bond with rhodium. The hydrogens are individually transfered to the double-bonded alkene resulting in a saturated product. [See R. T. Morrison et al *Organic Chemistry*, 4th Ed. Allyn and Bacon, Newton, Mass. (1983) pp. 335–339.]

"Solvent" is a liquid substance capable of dissolving or dispersing one or more other substances. It is not intended that the present invention be limited by the nature of the solvent used. In one embodiment, a solvent is used that is capable of solubilizing unreacted germane. In general, solvents such as benzene will suffice.

"Glass" is an amorphous crystalline material that has a wide range of viscosity values as a function of temperature. Unlike ordinary crystals that have a regular periodic lattice of atoms and a well-defined melting temperature, glass is an irregular suspension of molecules and has no well-defined melting temperature. For fiber-optics purposes, there are two general kinds of glass: 1) "fused silica" ($SiO_2$) to which dopant materials are added to change the index of refraction; and 2) "multicomponent glass" which is made up of a number of components, such as sodium borosilicate and soda lime silicate.

DESCRIPTION OF THE INVENTION

Figure 1:
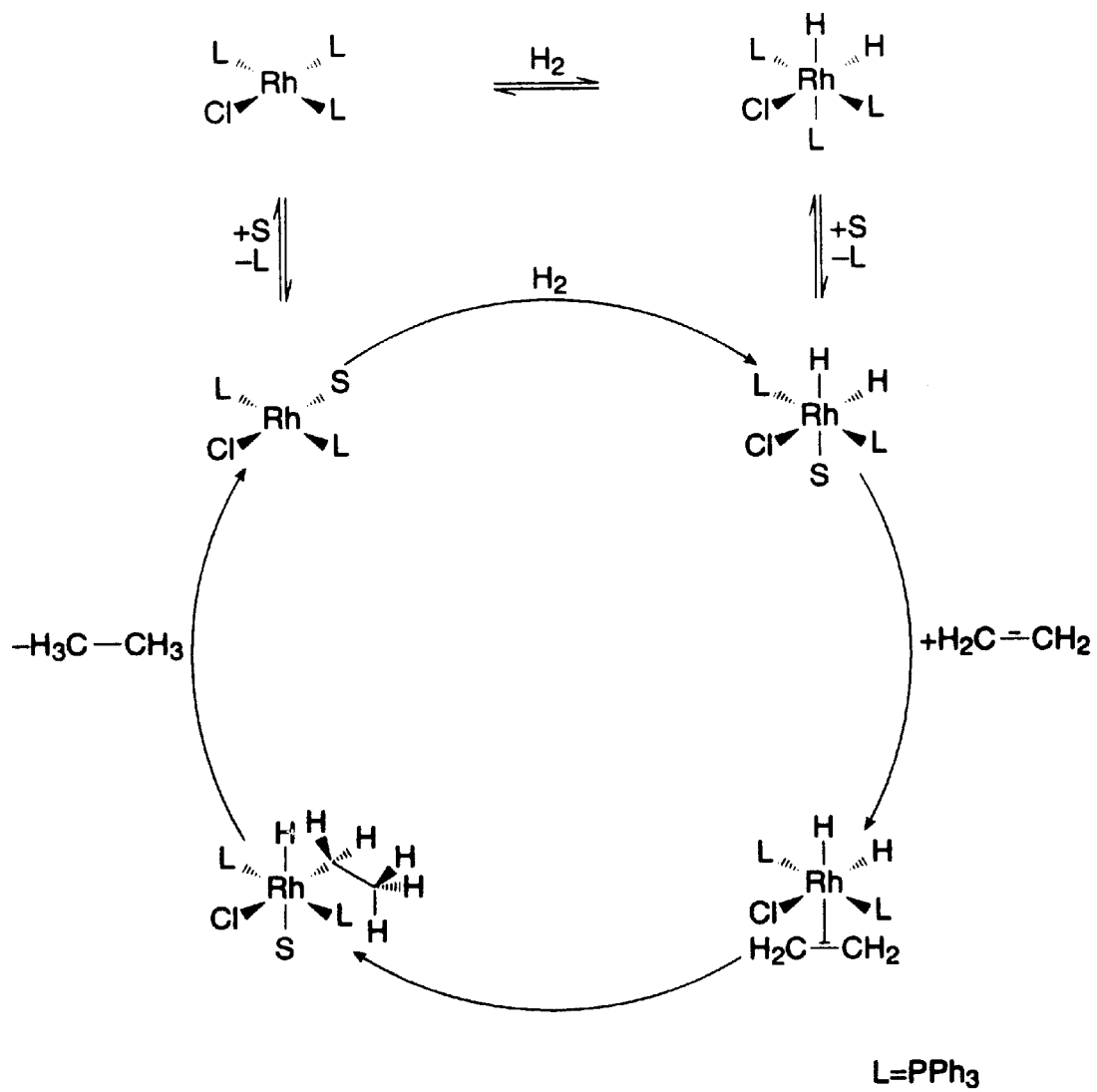
FIG. 1 is a schematic of one embodiment of the catalytic process for synthesizing novel germanes of the present invention.

The present invention relates to novel germanium-containing compounds and methods of using germanium-containing compounds. In particular, the present invention involves novel germanes and doping silicon-containing substrates, including polycrystalline silicon, with novel germanes.

A. Substrates

Silicon is the material used for the construction of computing microprocessors, and its fabrication technologies have developed at an unprecedented pace over the past 30 years. While this technology was initially applied to making microelectronic devices, the same techniques are currently being used for other devices.

As a substrate, silicon has well-known fabrication characteristics. The economic attraction of silicon devices is that their associated micromachining technologies are, essentially, photographic reproduction techniques. In these processes, transparent templates or masks containing opaque designs are used to photodefine objects on the surface of the silicon substrate. The patterns on the templates are generated with computer-aided design programs and can delineate structures with line-widths of less than one micron. Once a template is generated, it can be used almost indefinitely to produce identical replicate structures.

Other substrates, such as glass or quartz, can also use photolithographic methods to construct microfabricated analysis devices. Moreover, the present invention contemplates such substrates for particular applications of the germane doping methods of the present invention, such as applications for fiber fabrication.

B. Doping

In general, the ideal material for doping a substrate should have the following properties. First, the material should be cheap, easily prepared, easily applied, environmentally safe and functional. Currently several materials are used as a source for applying Ge to devices such as fiber optics and MOSFET, the major one being $GeCl_4$. $GeCl_4$ is indeed relatively inexpensive, easily applied and functional. However, applying this material results in the formation of some environmentally hazardous and unsafe byproducts, including HCl and chlorine gas.

The present invention provides for the manufacture of a new class of germanes, called bisamidegermanes, under catalytic conditions with no toxic by-products. The invention utilizes known, commercially available materials and very mild conditions with commercially acceptable yields.

In one embodiment, the present invention produces the novel germanes via catalytic hydrogenation of bisamidegermylenes. This invention relates to the process for the preparation of bisamidegermanes of the general formula $H_2Ge(NR_2)_2$, wherein R=alkyl, aryl, alkylaryl, trialkylsilyl, and the like. The present invention solves the problem of competitive side-reactions which involve breaking the Ge—N bond leading to the formation of undesired amines, as well as the problem of forming catenated Ge—Ge species. The process involves using transition metal catalysts of either (or a combination of) Co, Rh, Ir, Ni, Pd, and Pt with dihydrogen in contact with a bisamidegermylene. Furthermore, this invention is also directed to the preparation of bisamidegermanes of high purity.

The bisamidegermanes of the present invention are valuable as a general precursory material for a wide variety of substituted germanes. The inherent reactivity of germanium-amide groups offers a wider variety of possible modifications than existing germanes, greatly increasing the general range of applicability of such materials and their use in novel applications. For example, the amide groups can be easily replaced by carbon-based substituents, or they can be readily hydrolyzed forming condensation products having [—Ge—O—Ge—O] linkages similar to silicone polymers.

Indeed, the novel bisamidegermanes of the present invention are endowed with amide functionalities which impart useful chemical properties. These amide groups can be readily cleaved by hydrolysis, thus acting as chemical leaving groups. The Ge—H bond is also relatively weak making it susceptable to cleavage by chemical attack. These properties make the novel compounds of the present invention particularly useful as a Germanium doping source. In effect, the compounds of the present invention act as a $GeH_2$ synthon. In contrast to other bisamidegermanes, the preferred compounds of the present invention does not contain any Ge—C bonds. This is important because precursor materials should mimic on the molecular scale the stoichiometry of the desired end-product. That is to say, current bisamide germanes such as a dialkyl-bisamidegermane could put Germanium on a device, however it would contain a high carbon content, which is quite undesirable. It is believed that the present invention provides the only method currently available for preparing complexes which are stable yet contain both Ge—H and Ge—N bonds.

C. Preparation of Germanes

The present invention provides a process for the preparation of bisamidegermanes (or organogermanes) which process comprises contacting bisamidegermylenes (whether stable germylenes, or those generated in situ) with a catalyst in the presence of hydrogen according to the general equation:

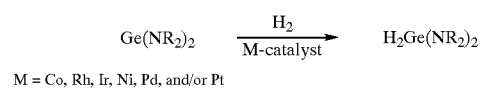

M = Co, Rh, Ir, Ni, Pd, and/or Pt

The method of the present invention involves the preparation of bisamidegermanes wherein bisamidegermylenes are coupled to dihydrogen by soluble low-valent metal catalysts. Preferred catalysts are those comprising known transition metal complexes of Co, Rh, Ir, Ni, Pd, and/or Pt to synthesize bisamidegermanes (of quite high purity) from bisamidegermylenes. In general, it has been found that the best catalyst for the manufacture of bisamidegermanes is bis-1,5-cyclooctadiene-nickel(0).

It has been found that if a bisamidegermylene is included in a mixture of a soluble Co, Rh, Ir, Ni, Pd, and/or Pt complex with hydrogen, bisamidegermanes are cleanly and efficiently prepared. The metal catalysts are generally employed from 1–10 mole% (can use more or less depending upon desired reaction time for completion) and afford suitably mild conditions for the formation of Ge—H bonds while minimizing undesired side-reactions and by-products.

FIG. 1 is a schematic of one embodiment of the catalytic process for synthesizing novel germanes of the present invention. The embodiment involves the use of tris(triphenylphosphine)chlororhodium, or Wilkinson's catalyst.

In a preferred embodiment of the process of the invention, a particular bisamidegermylene is used, which upon hydrogenation by the catalyst, forms the desired bisamidegermane. Examples of particularly useful bisamidegermylenes are: bis-bis((trialkylsilyl)amide)germylene. N-N'-tert-butylethylenediamidegermylene, and the like. A number of bisamidegermylenes are available commercially; for example, bis-bis(trimethylsilyl)amide)germylene is available from Gelest, Inc. (Tullytown, Pa.). In general, these bisamidegermylenes are used which are soluble in the particular reaction mixture that is prepared.

In the process of the invention, the bisamidegermylene can be added progressively, i.e. according as the reaction progresses, but usually the full amount is added at the beginning of the reaction, and preferably in excess. Hydrogen may be added stoichiometrically, or in excess i.e. under high pressure, but usually bubbling under 1 atm pressure is sufficient. The appropriate solvent is one such that all reagents are completely dissolved during the course of the reaction and the product precipitates upon formation, although solvation of the product is not entirely undesirable.

The bisamidegermane may, but is not required to, remain in the reaction mixture during the course of the reaction. Upon completion of the reaction, the inert organic solvent may be removed by reduced pressure distillation, or appropriate separation technique (filtration. etc.). The bisamidegermane can be separated and purified from the reaction mixture using any of several appropriate purification techniques such as recrystallization, sublimation, or the like, depending upon the physical properties of the bisamidegermane. Again, the appropriate pressure, inert organic solvent, and temperature may vary depending upon the physical properties of the desired bisamidegermane being manufactured.

EXPERIMENTAL

The following examples serve to illustrate certain preferred embodiments and aspects of the present invention and are not to be construed as limiting the scope thereof.

In the experimental disclosure which follows, the following abbreviations apply: atm (atmosphere); eq (equivalents); M (Molar); $\mu$M (micromolar); N (Normal); mol (moles); mmol (millimoles); $\mu$mol (micromoles); nmol (nanomoles); gm (grams); mg (milligrams); $\mu$g (micrograms); L (liters); ml (milliliters); $\mu$l (microliters); cm (centimeters); mm (millimeters); $\mu$m (micrometers); nm (nanometers); °C. (degrees Centigrade); Ci (Curies); $Et_3P$ (triethylphosphine); MW (molecular weight); OD (optical density); TMS (trimethylsilyl).

EXAMPLE 1

0.571 g (1.3 mmoles) of $Ge[N(TMS)_2]_2$ and 0.20 g (0.03 mmoles) of $(Et_3P)_2NiGe[N(TMS)_2]_2$ were dissolved in 25 mL of benzene while exposed to 1 atm dihydrogen gas with vigorous stirring. After 72 hours, the flask was degassed and solvent removed in vacuo. The reaction was virtually quantitative by $^1$H—NMR (85% by integration). The product was purified by sublimation at 0.001 torr in a 35° C. bath onto a 0° C. cold finger probe and collected in a 43% isolated yield as a colorless, viscous oil. $^1$H—NMR ($C_6D_6$) $\delta$ 0.27 ppm (s, 36H, TMS), 5.69 ppm (s, 2H, Ge—H); $^{13}$C—NMR ($C_6D_6$) $\delta$ 4.51 ppm (s, Si—$CH_3$); Analysis Calculated for $C_{12}H_{38}N_2GeSi_4$; C=36.5, H=9.68, N=7.08; Found C=35.74, H=9.24, N=6.91. IR Spectroscopy gave 2955, 2901, 2095, 2067, 1264, 1251, 936, 914, 881, 838, 786, 759, 716. High Resolution mass spectroscopy gave parent ion at 396 amu with isotopic distribution consistent with the calculated theoretical results.

EXAMPLE 2

0.571 g (1.3 mmoles) of Ge[N(TMS)$_2$]$_2$ and 0.008 g (0.03 mmoles) of bis(1,5-cyclooctadiene)nickel were dissolved in 25 mL of benzene while exposed to 1 atm dihydrogen gas with vigorous stirring. After 21 hours, the flask was degassed and solvent removed in vacuo. The reaction was quantitative by $^1$H—NMR (100% by integration). The product was purified by sublimation at 0.001 torr in a 40° C. bath onto a −78° C. cold finger probe and 0.352 g collected in a 61.3% isolated yield as a colorless, viscous oil. $^1$H—NMR and IR data matched that listed for the reaction in Example 1.

EXAMPLE 3

In this experiment, the ability of the bisamidegermanes of the present invention to act as a doping agent was tested by exposing the liquid bisamidegermane to a very fine silica gel powder having a known surface area and particle size. Specifically, under a nitrogen atmosphere 40 mg of H$_2$Ge [N(TMS)$_2$]$_2$ was allowed to coat 200–400 mesh (60 angstrom) silica gel (SiO$_2$) having a surface area (BET) of 500 m$^2$/g. After 2 hours, the mixture was rinsed with C$_6$D$_6$ and a $^1$H—nmr was taken of the filtrate. The data showed that unreacted bisamidegermane and a small amount of HN(TMS)$_2$ were present. IR spectroscopic analysis of the solid material suggested that Ge—O bonds were present at 836 cm$^{-1}$ and 941 cm$^{-1}$ and that the surface bound material still contained trimethylsilyl groups as evidenced by the peaks at 2952, 2917, 2847, 878, 787 cm$^{-1}$. Elemental analysis confirmed the presence of trimethylsilyl amide groups, analysis gave C=12.89%, H=3.89%, and N=1.93% a molar ratio pf 7.9:28:1 compares to the expected 6:18:1 CHN ratio respectively. The hydrogen ratio is high due to absorbed water. The presence of Ge on the silica is confirmed by the X-ray photoelectron spectra (XPS) showing the Ge 2p$_{3/2}$, at 1218.6 eV. Ge 3p at 127 eV, Ge 3d at 31.9 eV. The standard for GeO$_2$ demonstrates that the new surface bound material is not GeO$_2$, nor is it the initial material. While an understanding of the precise interaction is not necessary to successful use of the invention, the group electronegativities suggest that the bisamidegermane may have bound to the surface by one or more of the former Ge—H bonds. This can be readily converted to GeO$_2$ by hydrolysis, leaving a Ge—O coated silica surface. Overall, the surface area calculations show 1.67 to 1.58 molecules/nm$^2$ of germane on the surface.

EXAMPLE 4

Figure 2:
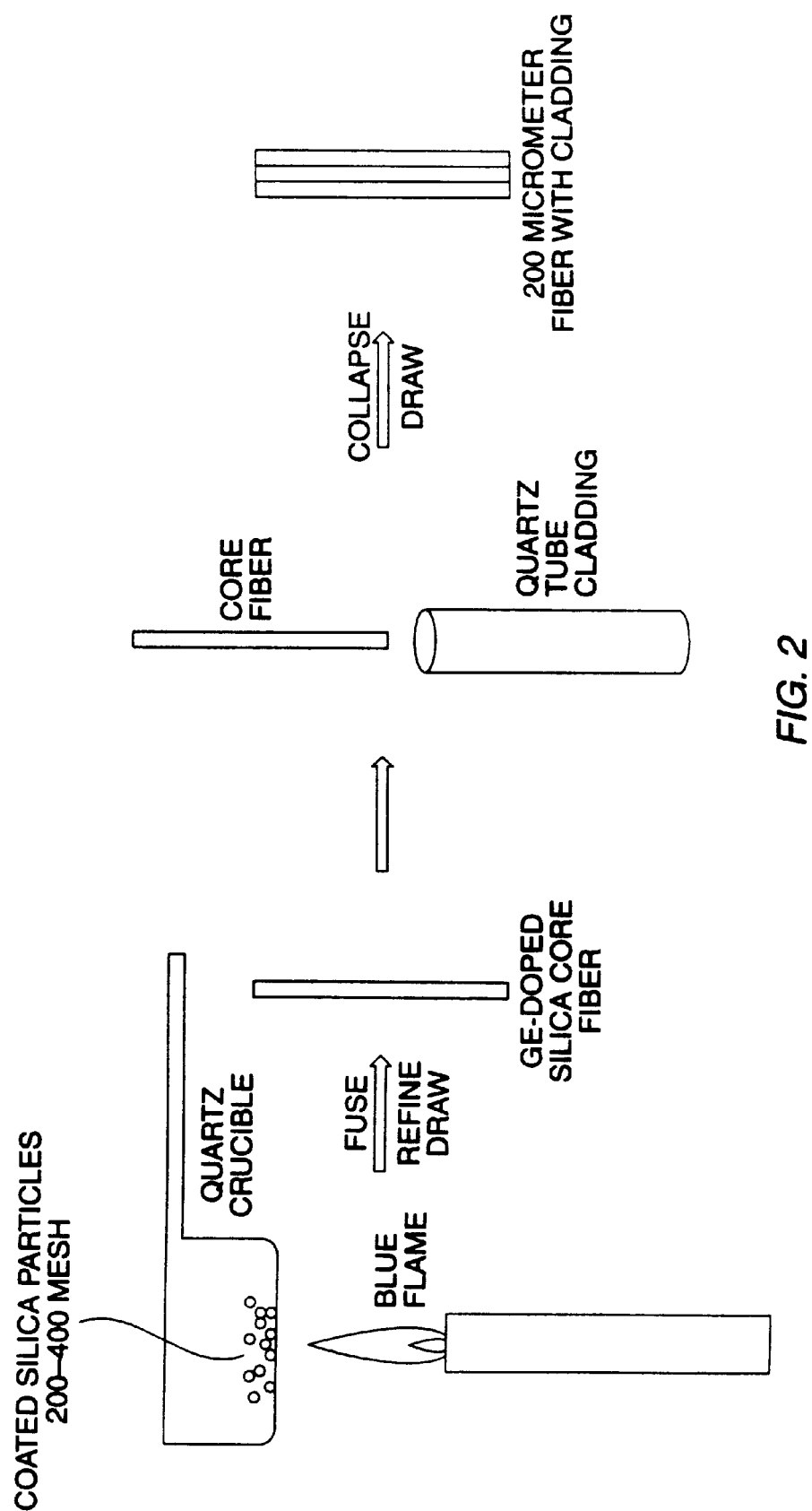
FIG. 2 shows the construction of a silicon device doped according to one embodiment of the method of the present invention.

In this experiment, the germanium-containing compounds of the present invention were utilized to prepare material for a fiber optic device. First, 500 mg of coated silica was prepared as described above in Example 3. This coated silica was then heated in a quartz cubicle (see FIG. 2) until the silica became fused (about 1500° C.). This was then refined and drawn several times until the gas bubbles were no longer visible. A core fiber was then drawn from this clear fixed-silica-Ge-doped glass having a 2 mm OD and then heated until the cladding tube collapsed around the core. This was then drawn until a 200 micrometer fiber was obtained. From these results, it is clear that the bisamidegermanes of the present invention are indeed useful for doping silicon-containing materials and these materials may be used for fiber optic and related devices.

EXAMPLE 5

As noted previously, silicon-containing substrates have well-known fabrication characteristics and associated photographic reproduction techniques. The principal modem method for fabricating semiconductor integrated circuits is the so-called planar process. The planar process relies on the unique characteristics of silicon and comprises a complex sequence of manufacturing steps involving deposition, oxidation, photolithography, diffusion and/or ion implantation, and metallization, to fabricate a "layered" integrated circuit device in a silicon substrate. See e.g., W. Miller, U.S. Pat. No. 5,091,328, hereby incorporated by reference.

For example, oxidation of a crystalline silicon substrate results in the formation of a layer of silicon dioxide on the substrate surface. Photolithography can then be used to selectively pattern and etch the silicon dioxide layer to expose a portion of the underlying substrate. These openings in the silicon dioxide layer allow for the introduction ("doping") of ions ("dopant") into defined areas of the underlying silicon. The silicon dioxide acts as a mask; that is, doping only occurs where there are openings. Careful control of the doping process and of the type of dopant allows for the creation of localized areas of different electrical resistivity in the silicon.

In this example, the doping of the silicon dioxide is done without photolithography. Instead, the silicon dioxide is coated as in Example 3 above. Thereafter, the germanium-coated material is employed in the planar process to make a layer of germanium-doped silicon dioxide.

From the above it should be evident that the present invention provides germanium-containing compounds which can function as dopants and where the methods for their use are flexible, reliable and environmentally safe. The process overcomes several difficulties in the synthesis of germanes, specifically the use of expensive reducing agents, corrosive starting materials, and the numerous side-reactions which result from their use. Furthermore, the process involves utilizing readily obtainable transition-metal reagents in very small amounts which can be continually re-used until contaminated.

We claim:

1. A germanium-containing compound of the general formula:

H$_2$Ge(NR$_2$)$_2$, wherein R=alkyl, aryl, alkylaryl, or trialkylsilyl.

2. The germanium-containing compound of claim 1, wherein R is trimethylsilyl.

3. A method of synthesizing a germanium-containing compound, comprising contacting one or more bisamidegermylenes with a catalyst in the presence of hydrogen, under conditions such that one or more bisamidegermanes are produced.

4. The method of claim 3, wherein said bisamidegermane is of the general formula:

H$_2$Ge(NR$_2$)$_2$, wherein R=alkyl, aryl, alkylaryl, or trialkylsilyl.

5. The method of claim 4, wherein R is trimethylsilyl.

6. The method of claim 3, wherein said catalyst is a transition metal catalyst.

7. The method of claim 6, wherein the transition metal of said transition metal catalyst is selected from the group consisting of Co, Rh, Ir, Ni, Pd, and Pt.

8. The method of claim 6, wherein said catalyst is Wilkinson's catalyst.

9. The method of claim 6, wherein said catalyst is bis(1,5-cyclooctadiene)nickel.

10. The method of claim 3, wherein said bisamidegermylene is a bis-bis((trialkylsilyl)amide)germylene.

11. The method of claim 10, wherein said bis-bis((trialkylsilyl)amide)germylene is bis-bis((trimethylsilyl)amide)germylene.

12. The method of claim 3, wherein said bisamidegermylene is N-N'-tert-butylethylenediamidegermylene.

13. A method of doping a silicon-containing substrate, comprising exposing a liquid germane to a dry silicon-containing substrate, under conditions such that a doped substrate is produced.

14. The method of claim 13, wherein said silicon-containing substrate comprises silicon dioxide.

15. The method of claim 13, wherein said germane is a bisamidegermane of the general formula: $H_2Ge(NR_2)_2$, wherein R=alkyl, aryl, alkylaryl, or trialkylsilyl.

16. The method of claim 15, wherein R is trimethylsilyl.

17. The method of claim 13, further comprising the step of separating said doped substrate from said liquid germane so as to create a treated substrate.

18. The method of claim 17, wherein said separating is achieved by washing said doped substrate with a solvent.

19. The method of claim 18, wherein said solvent is benzene.

20. The method of claim 17, further comprising the step of heating said treated substrate.

* * * * *